(12) United States Patent
Van Brunt

(10) Patent No.: US 6,415,791 B1
(45) Date of Patent: *Jul. 9, 2002

(54) AIRWAY TREATMENT APPARATUS WITH COUGH INDUCEMENT

(75) Inventor: Nicholas P. Van Brunt, White Bear Lake, MN (US)

(73) Assignee: American Biosystems, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,457

(22) Filed: Oct. 4, 1999

(51) Int. Cl.$^7$ .............................................. A61M 16/00
(52) U.S. Cl. .............................. 128/204.18; 128/200.24
(58) Field of Search ...................... 601/41–44, 149–152, 601/148; 128/204.18, 204.21, 200.24, 202.12, 2.26; 237/46, 50; 239/429–434; 600/529, 532, 533

(56) References Cited

U.S. PATENT DOCUMENTS

| | | | | |
|---|---|---|---|---|
| 402,779 A | * | 5/1889 | Steinhoff | 601/41 |
| 2,354,397 A | | 7/1944 | Miller | 128/30 |
| 2,436,853 A | * | 3/1948 | Coleman | 601/43 |
| 2,588,192 A | | 3/1952 | Akerman et al. | 128/29 |
| 2,626,601 A | | 1/1953 | Riley | 128/38 |
| 2,762,366 A | | 9/1956 | Huxley, III et al. | 128/30 |
| 2,772,673 A | | 12/1956 | Huxley, III | 128/30 |
| 2,779,329 A | | 1/1957 | Huxley, III et al. | 128/30 |
| 2,780,222 A | | 2/1957 | Polzin et al. | 128/30 |
| 2,818,853 A | | 1/1958 | Huxley, III et al. | 128/30 |
| 2,832,335 A | | 4/1958 | Huxley, III et al. | 128/30 |
| 2,869,537 A | | 1/1959 | Chu | 128/27 |
| 3,043,292 A | | 7/1962 | Mendelson | 128/30 |
| 3,063,444 A | | 11/1962 | Jobst | 128/39 |
| 3,120,228 A | | 2/1964 | Huxley, III | 128/30 |
| 3,310,050 A | | 3/1967 | Goldfarb | 128/41 |
| 3,333,581 A | | 8/1967 | Robinson et al. | 128/30.2 |
| 3,536,063 A | | 10/1970 | Werding | 128/24 |
| 3,566,862 A | | 3/1971 | Schuh | 128/30 |
| 3,683,655 A | | 8/1972 | White et al. | 128/30.2 |
| 3,742,939 A | | 7/1973 | Sayer | 600/538 |
| 3,760,801 A | | 9/1973 | Borgeas | 128/25 |
| 3,802,417 A | | 4/1974 | Lang | 128/2 |
| 3,896,794 A | | 7/1975 | McGrath | 128/24 |
| 3,993,053 A | | 11/1976 | Grossan | 128/64 |
| 4,051,843 A | | 10/1977 | Franetzki et al. | 600/538 |
| 4,079,733 A | | 3/1978 | Denton et al. | 128/55 |
| 4,133,305 A | | 1/1979 | Steuer | 128/33 |
| 4,311,135 A | | 1/1982 | Brueckner et al. | 128/24 |
| 4,349,015 A | * | 9/1982 | Alferness | 128/28 |
| 4,397,306 A | | 8/1983 | Weisfeldt | 601/41 |
| 4,398,531 A | | 8/1983 | Havstad | 128/55 |
| 4,424,806 A | | 1/1984 | Newman et al. | 128/28 |
| 4,429,688 A | | 2/1984 | Duffy | 128/28 |
| 4,546,764 A | | 10/1985 | Gerber | 128/33 |
| 4,621,621 A | | 11/1986 | Marsalis | 128/30.2 |
| 4,676,232 A | | 6/1987 | Olsson et al. | 128/28 |
| 4,815,452 A | | 3/1989 | Hayek | 128/302 |
| 4,838,263 A | | 6/1989 | Warwick et al. | 128/30.2 |
| 4,886,057 A | | 12/1989 | Nave | 128/203.11 |
| 4,928,674 A | | 5/1990 | Halperin et al. | 128/30.2 |

(List continued on next page.)

FOREIGN PATENT DOCUMENTS

EP 0 542 383 A2 5/1993

*Primary Examiner*—John G. Weiss
*Assistant Examiner*—Teena Mitchell
(74) *Attorney, Agent, or Firm*—Kinney & Lange

(57) ABSTRACT

An airway clearance system and method produces high frequency chest wall oscillations (HFCWO) and increased airflow velocities through the air passages to clear the lungs of mucus. The system includes a chest wall force applicator to produce the HFCWO, and an air pressure input mouthpiece system that enhances airflow to and from the patient's lungs and a simulated cough inducer that causes a cough-like airflow pattern during each oscillatory cycle.

63 Claims, 12 Drawing Sheets

U.S. PATENT DOCUMENTS

| | | | | |
|---|---|---|---|---|
| 4,971,042 A | * | 11/1990 | Lerman | 601/41 |
| 4,977,889 A | | 12/1990 | Budd | 128/30.2 |
| 4,982,735 A | | 1/1991 | Yagata et al. | 128/204.23 |
| 5,056,505 A | | 10/1991 | Warwick et al. | 128/30.2 |
| 5,076,259 A | | 12/1991 | Hayek | 128/30.2 |
| 5,101,808 A | | 4/1992 | Kobayashi et al. | 128/30.2 |
| 5,193,745 A | | 3/1993 | Holm | 239/102.2 |
| 5,222,478 A | | 6/1993 | Scarberry et al. | 128/30.2 |
| 5,261,394 A | | 11/1993 | Mulligan et al. | 128/55 |
| 5,299,599 A | | 4/1994 | Farmer et al. | 137/625.22 |
| 5,453,081 A | | 9/1995 | Hansen | 601/150 |
| 5,455,159 A | | 10/1995 | Mulshine | 435/7.23 |
| 5,492,115 A | * | 2/1996 | Abramov et al. | 128/205.24 |
| 5,569,122 A | | 10/1996 | Cegla | 482/13 |
| 5,606,754 A | | 3/1997 | Hand et al. | 5/713 |
| 5,720,709 A | | 2/1998 | Schnall | 600/538 |
| 5,769,797 A | | 6/1998 | Van Brunt et al. | 601/41 |
| 5,806,512 A | * | 9/1998 | Abramov et al. | 128/204.28 |
| 5,891,062 A | | 4/1999 | Schock | 601/41 |
| 5,910,071 A | | 6/1999 | Hougen | 482/13 |
| 5,997,488 A | * | 12/1999 | Gelfand et al. | 601/41 |
| 6,030,353 A | | 2/2000 | Van Brunt | 601/150 |
| 6,066,101 A | | 5/2000 | Johnson et al. | 600/533 |
| 6,068,602 A | | 5/2000 | Tham et al. | 600/533 |
| 6,210,345 B1 | * | 4/2001 | Van Brunt | 600/529 |

* cited by examiner

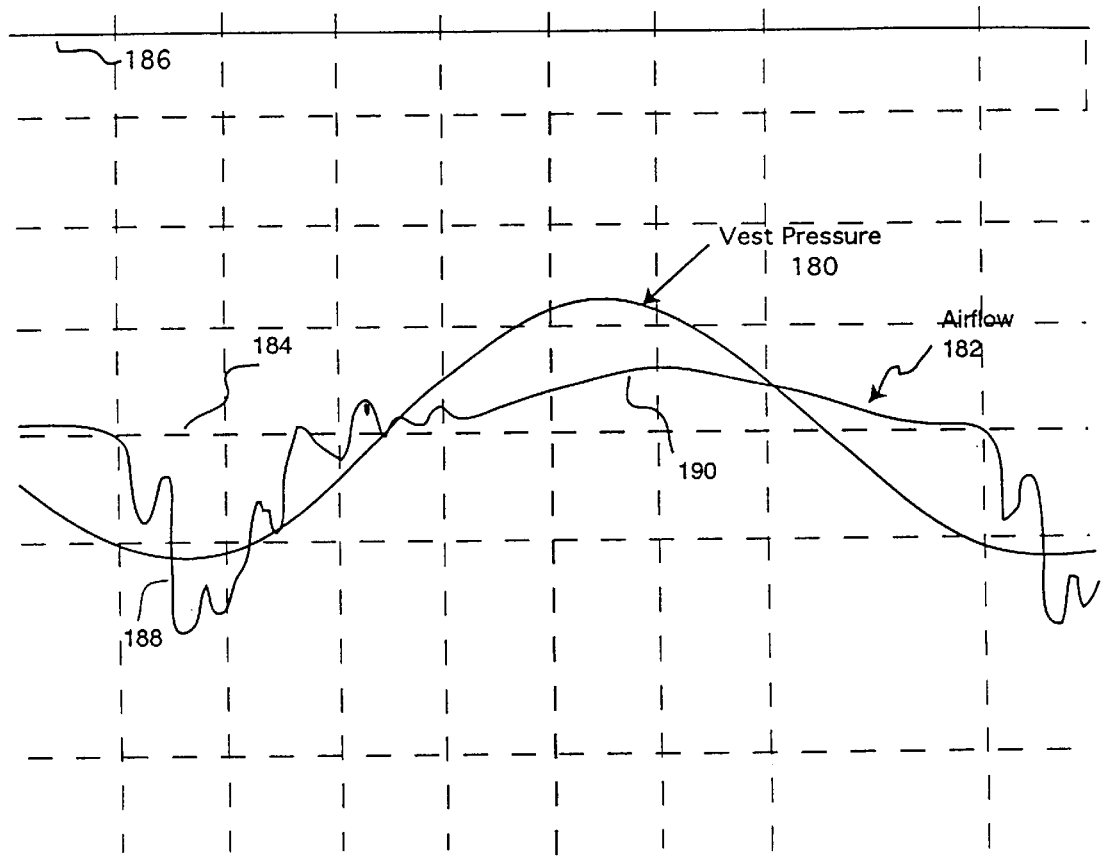
mouth flow= 2 liter/sec/division
vest pressure= 0.1 psi/division
cycle period=13 hz
FIG. 4-a

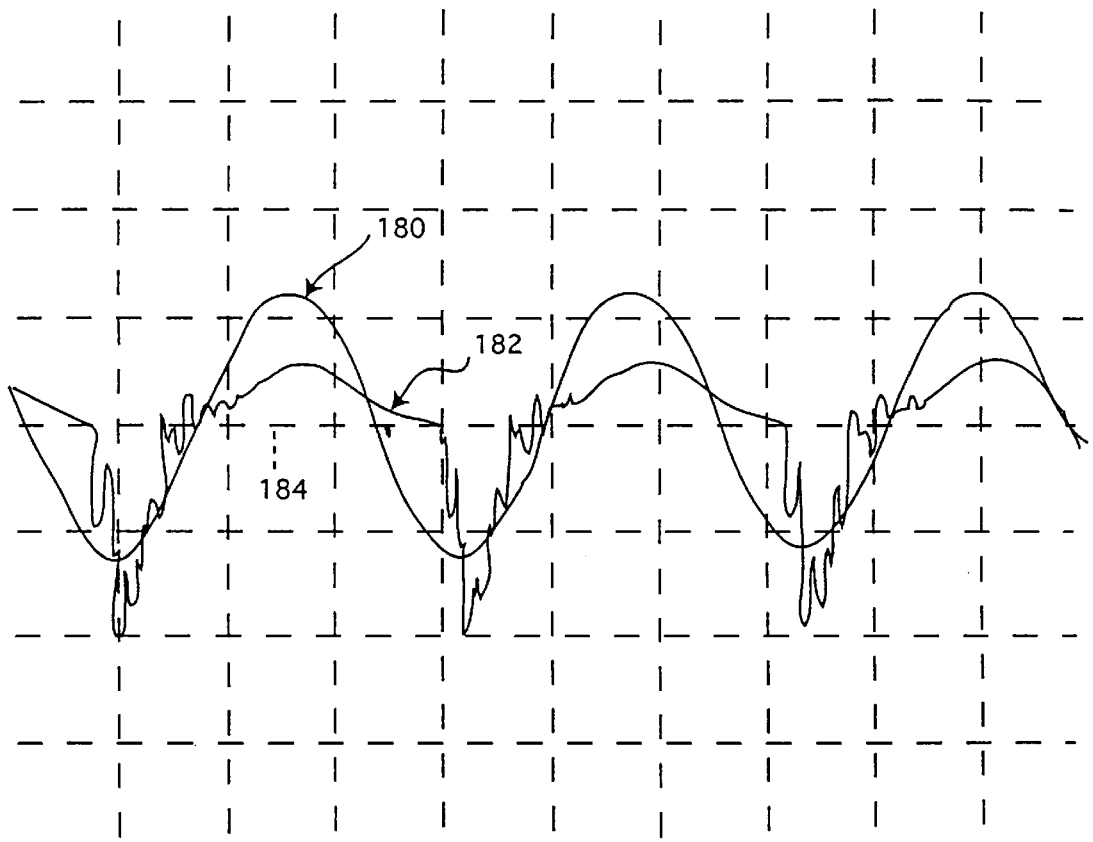
FIG. 4-b

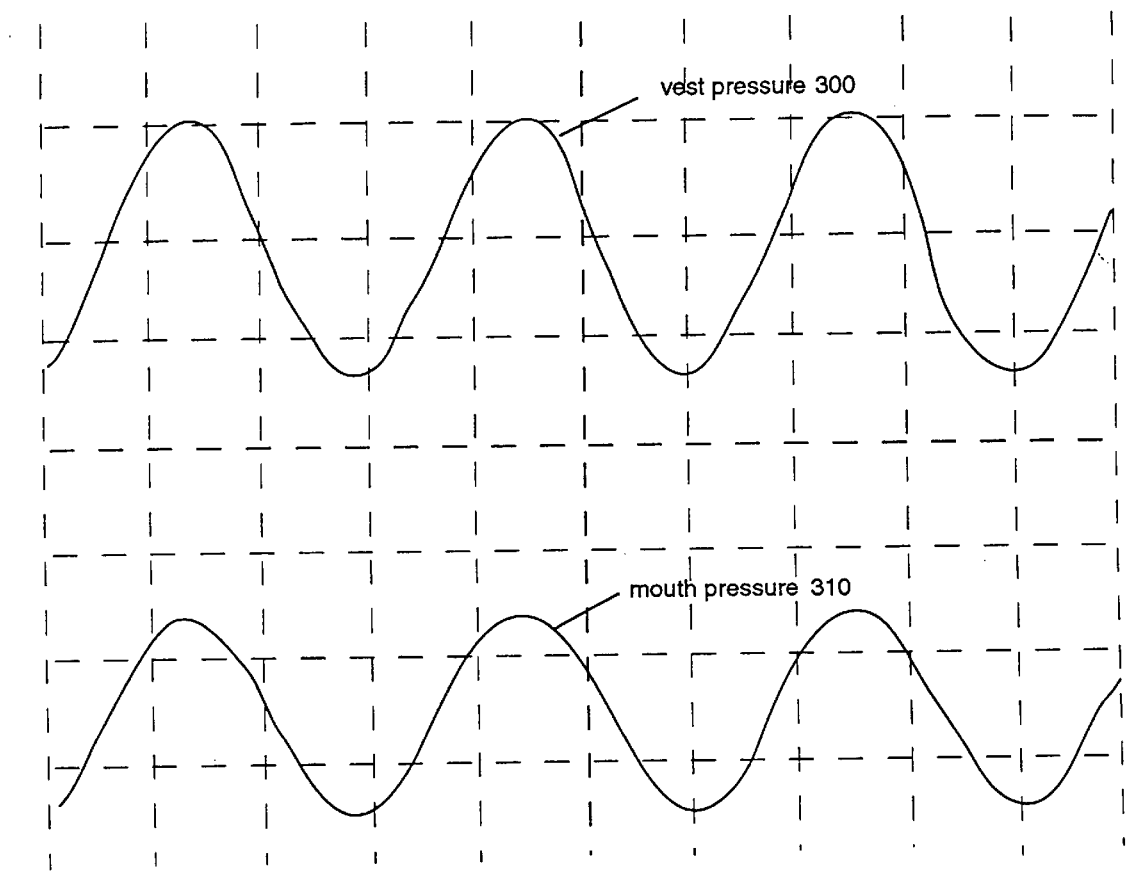
FIG. 8-a

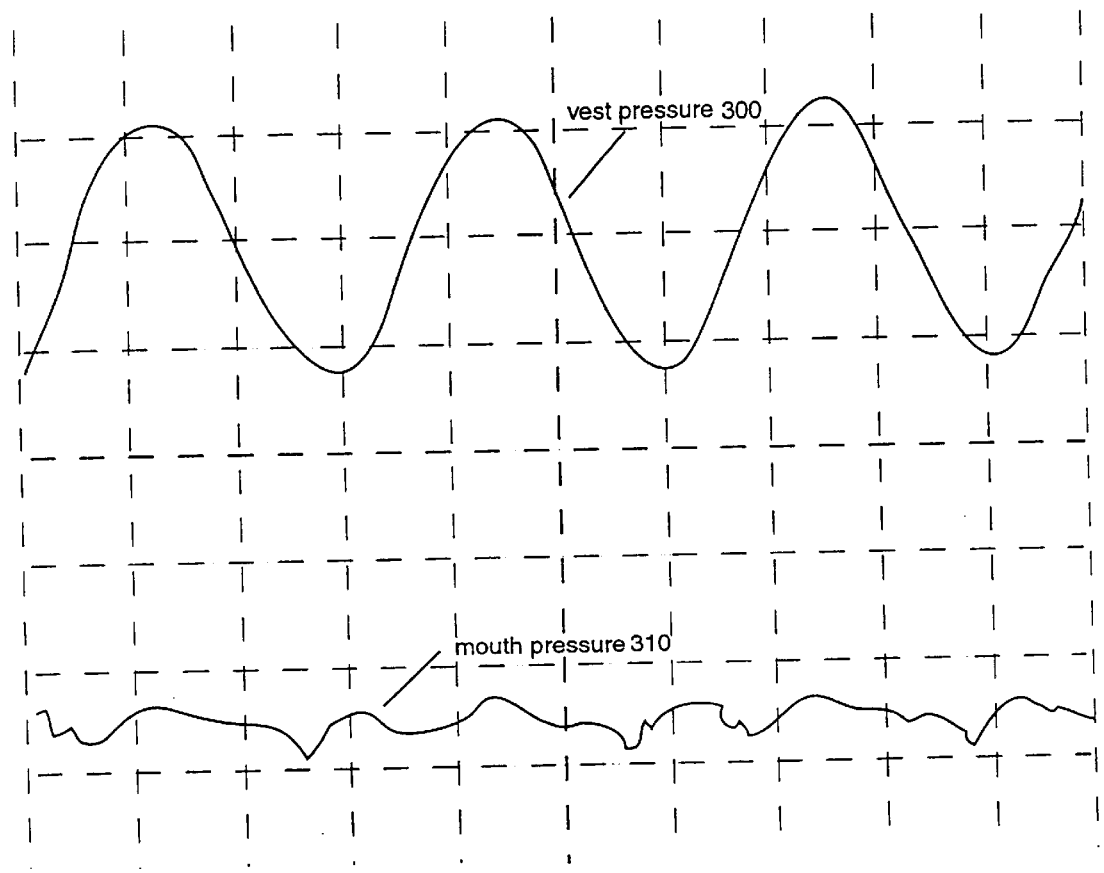
FIG. 8-b

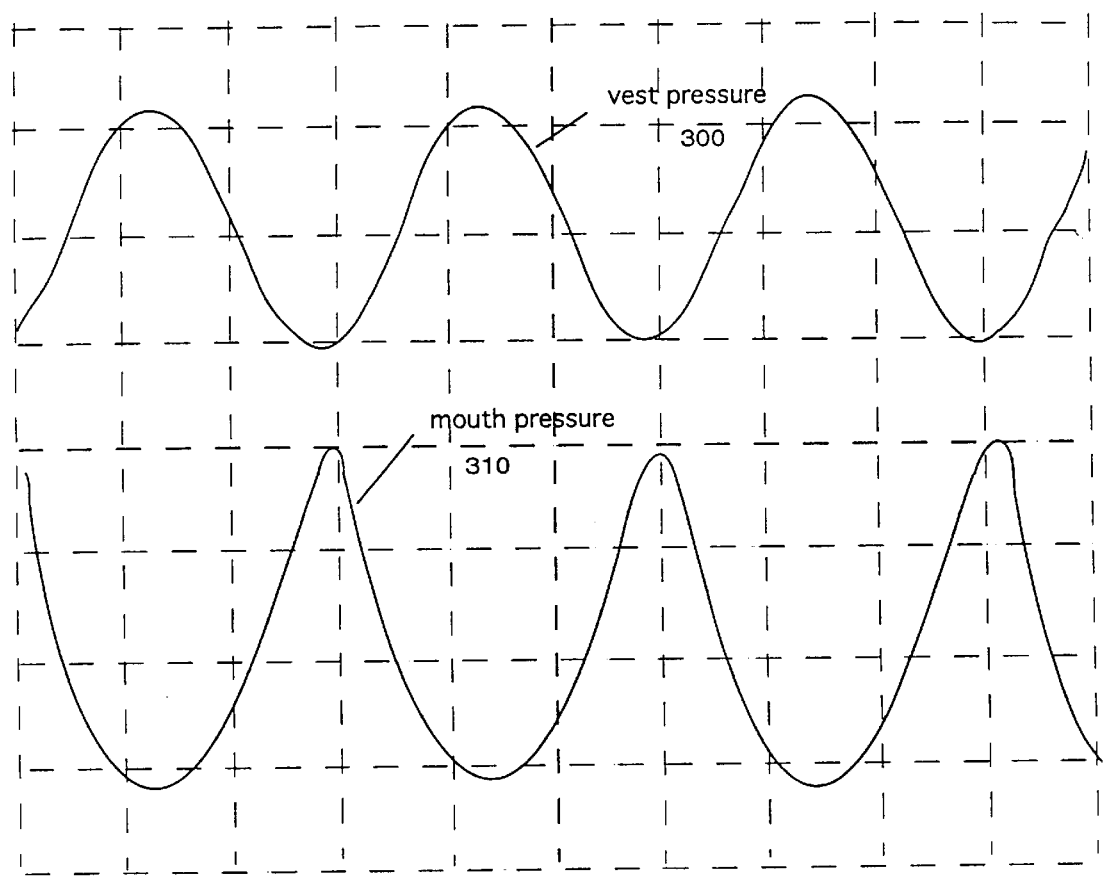
FIG. 8-c

AIRWAY TREATMENT APPARATUS WITH COUGH INDUCEMENT

CROSS-REFERENCE TO RELATED APPLICATION(S)

Reference is made to the following copending applications which are filed on even date and assigned to the same assignee as this application: AIRWAY TREATMENT APPARATUS WITH AIRFLOW ENHANCEMENT, Ser. No. 09/412,768; AIRWAY TREATMENT APPARATUS WITH BIAS LINE CANCELLATION, Ser. No. 09/412,459; and OUTCOME MEASURING AIRWAY RESISTANCE DIAGNOSTIC SYSTEM, U.S. Pat. No. 6,210,345.

BACKGROUND OF THE INVENTION

The present invention relates to an airway clearance system and in particular to a system that includes a chest compression device for high frequency chest wall oscillation and a subsystem which induces simulated coughs and enhances airflow velocity through the air passages caused by the high frequency chest wall oscillations.

Chest compression devices have been developed to produce high frequency chest wall oscillation (HFCWO). HFCWO is the most successful method used for removing excess mucus from the lungs caused by a variety of diseases such as cystic fibrosis, emphysema, asthma, chronic obstructive pulmonary disease (COPD), and chronic bronchitis.

The device most widely used to produce HFCWO is the ABI Vest™ Airway Clearance System by American Biosystems, the assignee of the present application. A description of the pneumatically driven system can be found in the Van Brunt et al. patent, U.S. Pat. No. 5,769,797, which is assigned to American Biosystems. Another example of a pneumatic chest compression vest has been described by Warwick et al., U.S. Pat. No. 4,838,263.

Pneumatically driven HFCWO produces substantial transient increases in the airflow velocity with a small displacement of the chest cavity volume. This action produces a cough-like shear force and reduction in mucus viscosity that results in an upward motion of the mucus. The ABI Vest Airway Clearance System is effective in clearing airways of mucus, however, there are limitations of its performance.

There is a constant vest pressure on the chest of the patient when using the vest. This can cause particular problems with some disease states. External pressure on the chest of a COPD patient during inspiration may cause considerable distress. Also, asthmatics may find the constant vest pressure extremely irritating, and those with constricted and inflamed airways may find it uncomfortable. Therefore, eliminating the constant vest pressure would be beneficial.

It is difficult to determine a short term reduction in airway resistance during treatment. Airway resistance is the ratio of airway pressure to airway airflow. It is an indicator of the degree of plugging of the lung passages by mucus, and therefore, periodic measurement of airway resistance provides a good indicator of the success or lack thereof of a treatment for lung clearance.

Prior art vest systems do not have the ability to aid in removing mucus from the upper airway passages. With some disease states, the debilitated patient is unable to produce a cough to remove the mucus accumulated in the upper airway passages. Normally, the current vest systems accelerate the mucus upward and outward in the upper bronchial passages and trachea by increasing airflow velocity. Many individuals can then, by means of a volitional cough, force the mucus into the mouth and then expectorate. The effectiveness of the treatment is greatly reduced if a weakened individual is unable to do this. Also, since a cough is an effective natural method of moving the mucus out of the airway, it would be beneficial to have a system which produced a cough on each oscillation of the chest wall.

Since increased airflow velocity is key to clearing the lungs of mucus, it would be advantageous to improve upon the current systems in order to induce even higher airflow velocities from users. This would make the vest system even more effective at removing mucus from the lungs.

BRIEF SUMMARY OF THE INVENTION

The invention is a method and apparatus for clearing a patient's lungs of mucus. An oscillating compressive force is applied to the patient's chest that includes a steady state force and an oscillating force component. Air pressure is supplied to the patient's mouth via a mouthpiece in a timed relationship to the oscillating compressive force to induce a simulated cough during a compressive force oscillatory cycle.

BRIEF DESCRIPTION OF THE DRAWINGS

FIG. 4a shows one oscillation of the chest wall force applicator pressure and airflow velocity during a simulated cough sequence.

FIG. 4b shows multiple oscillations of the chest wall force applicator pressure and airflow velocity during simulated cough sequences.

FIG. 8a is a graph of pressure waves during chest compression treatment from a chest wall force applicator and at a mouthpiece when the pressure at the mouthpiece is less than pressure produced by the chest wall force applicator.

FIG. 8b is a graph of pressure waves during chest compression treatment from the chest wall force applicator and at the mouthpiece when the pressure at the mouthpiece is at null.

FIG. 8c is a graph of pressure waves during chest compression treatment from the chest wall force applicator and at the mouthpiece when pressure at the mouthpiece is greater than pressure produced by the chest wall force applicator.

DETAILED DESCRIPTION

FIRST EMBODIMENT (FIG. 1)

Figure 1:
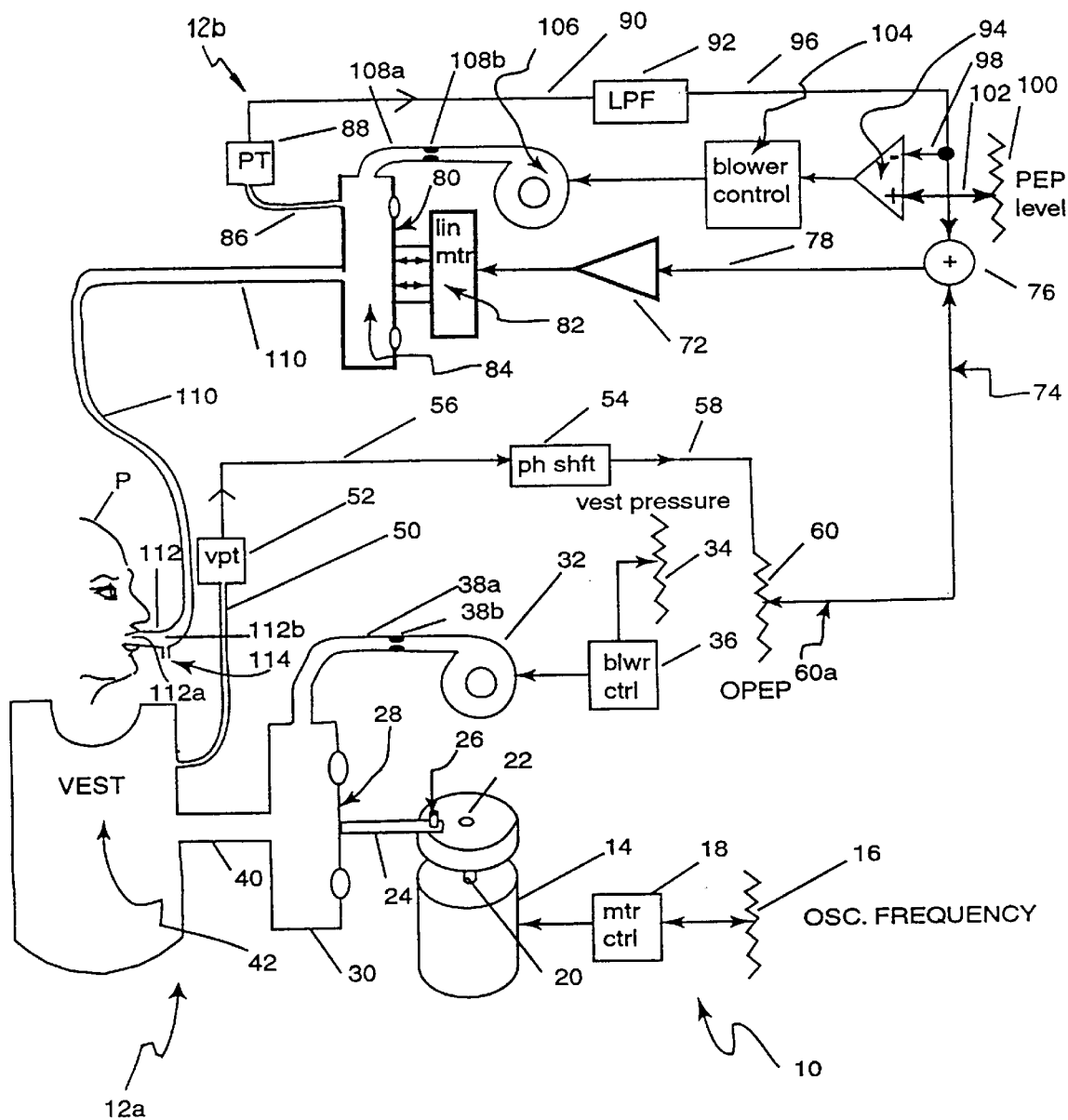
FIG. 1 shows a block diagram of a first embodiment which provides enhanced airway flow and chest compression bias line cancellation.

FIG. 1 is a block diagram showing a patient P undergoing treatment using the preferred embodiment of airway treatment apparatus 10. As shown in FIG. 1, apparatus 10 has two major subsystems, chest wall force applicator 12a (which applies oscillating compressive force to the chest of patient P) and air pressure input mouthpiece system 12b (which supplies air pressure to the patient's mouth in a relationship to the compressive force).

Chest wall force applicator 12a includes brushless motor 14, vest oscillation frequency potentiometer 16, motor controller 18, shaft 20, wheel 22, reciprocating arm 24, pin 26, diaphragm 28, air chamber 30, blower 32, vest pressure potentiometer 34, blower controller 36, tube 38a with constriction 38b, hoses 40, and inflatable vest 42. Oscillated air pressure is delivered to inflatable vest 42 to cause inflatable vest 42 to apply an oscillating force to the patient's chest.

Brushless motor 14 is operated by motor controller 18 at a speed which is set by vest oscillation frequency potentiometer 16. Shaft 20 is connected to brushless motor 14 and wheel 22. Reciprocating arm 24 is coupled to wheel 22 by pin 26, which is offset from the center of wheel 22. Reciprocating arm 24 is also coupled to diaphragm 28, which is part of air chamber 30.

Blower 32 is operated by blower controller 36 based upon a control setting of potentiometer 34. Tube 38a with constriction 38b couples blower 32 with air chamber 30. Hoses 40, in turn, couple air chamber 30 with inflatable vest 42.

The force generated on the patient's chest by chest wall force applicator 12a has an oscillatory air pressure component and a steady state air pressure component. In a preferred embodiment, the steady state air pressure (or "bias line pressure") is greater than atmospheric pressure, and the oscillatory air pressure rides on the steady state air pressure. With this embodiment, a whole oscillation of chest wall force applicator 12a is effective at moving the patient's chest, because there is no point at which pressure applied to the chest by vest 42 is below atmospheric pressure. Chest movement can only be induced while chest wall applicator 12a has an effective pressure (i.e. greater than atmospheric pressure) on the patient's chest.

The oscillatory air pressure component is created by brushless motor 14. The speed of brushless motor 14 is selected by vest oscillation potentiometer 16 and held constant by motor controller 18. Shaft 20 of brushless motor 14 rotates wheel 22 which, in turn, moves reciprocating arm 24 in a linear fashion and causes diaphragm 28 to oscillate the air in air chamber 30 at a frequency selected by vest oscillation potentiometer 16. The pressure created by brushless motor 14 follows a sinusoidal waveform pattern.

To create the steady state air pressure, vest pressure potentiometer 34 selects the speed of blower 32 and the speed is held constant by blower controller 36. The steady state air pressure is transferred to air chamber 30 through tube 38a. Constriction 38b within tube 38a prevents backflow of pressure pulses into blower 32 which would affect the pressure pulsation in a nonlinear manner. In effect, constriction 38b is a large impedance to oscillatory airflow but a low impedance to steady state airflow. The steady state air pressure created by blower 32 is greater than atmospheric pressure so that a whole oscillatory cycle is effective at moving the patient's chest. Preferably, blower 32 has a pressure maximum of 12 cm of water, which is well within tolerance limits of anticipated users. This is a safety feature designed so that if any component failure tended to speed up blower 32, it would not be unsafe.

Hoses 40 convey air pressure waves from air chamber 30 to inflatable vest 42. Inflatable vest 42, thus, is cyclically inflated and deflated to apply HFCWO to the patient's chest at a frequency set by vest oscillation frequency potentiometer 16 about a steady state or bias line pressure set by vest pressure potentiometer 34. The steady state air pressure determines the intensity of the chest compressions since the oscillatory air pressure rides on the steady state air pressure. Therefore, the change of pressure (delta pressure) increases with increasing steady state pressure and results in the oscillatory air pressure never being less than atmospheric pressure. In applying HFCWO to the patient's chest, the patient's airways are cleared of mucus.

Chest wall force applicator 12a also includes components to link it to air pressure input mouthpiece system 12b. These include vest sampling tube 50, vest pressure transducer (VPT) 52, phase shift network 54, line 56, line 58, and Oscillatory Positive Expiratory Pressure (OPEP) oscillation intensity potentiometer 60.

Vest sampling tube 50 is connected to inflatable vest 42 at one end and vest pressure transducer 52 at the other end. Vest pressure transducer 52 is connected to phase shift network 54 via line 56. Line 58 then connects phase shift network 54 to OPEP potentiometer 60.

In operation, vest sampling tube 50 conveys vest pressure to vest pressure transducer 52 which converts it to an electrical signal representative of ensued vest pressure. The electrical output signal of vest pressure transducer 52 is sent to phase shift network 54 via line 56. Phase shift network 54 compensates for delays in oscillatory pressure from chest wall force applicator 12a being transmitted as an oscillation within the patient's lungs and to the patient's mouth. The signal from phase shift network 54 (having a waveform representative of vest pressure applied by chest wall force applicator 12a) is supplied by line 58 to OPEP potentiometer 60 and then to air pressure input mouthpiece system 12b.

Air pressure input mouthpiece system 12b includes motor drive amplifier 72, line 74, summing junction 76, line 78, diaphragm 80, linear motor 82, air chamber 84, sampling tube 86, pressure transducer(PT) 88, line 90, low pass filter (LPF) 92, comparator error amplifier 94, line 96, line 98, Positive Expiratory Pressure (PEP) level potentiometer 100, line 102, blower controller motor driver 104, blower 106, tube 108a with constriction 108b, tube 110, and mouthpiece 112 (with mouth port 112a, air supply port 112b, and outlet port 114).

Wiper 60a of OPEP potentiometer 60 is connected to motor drive amplifier 72 via line 74, summing junction 76, and line 78. Motor drive amplifier 72 is connected to diaphragm 80 of linear motor 82. Diaphragm 80 is then connected with air chamber 84 which is coupled to sampling tube 86 followed by pressure transducer 88. Line 90 connects pressure transducer 88 to low pass filter 92 which is followed by a connection to summing junction 76 and to comparator error amplifier 94 via lines 96 and 98. Comparator error amplifier 94 is also connected to PEP level potentiometer 100 through line 102 and to blower controller motor driver 104. Blower controller motor driver 104 provides a drive signal to blower 106, which is coupled to air chamber 84 by tube 108a that contains constriction 108b. Tube 110 extends from air chamber 84 and connects to air supply port 112b of mouthpiece 112. Mouth port 112a of mouthpiece 112 is placed in communication with the patient's mouth (i.e. either in or over the mouth). Mouthpiece 112 may also cover the patient's nose. Outlet port 114 is located a short distance from mouthpiece 112 on tube 110.

In operation, the processed pressure waveform from vest pressure transducer 52 and phase shift network 54 is input to OPEP potentiometer 60 as described above. OPEP potentiometer 60 adjusts an Oscillatory Positive Expiratory Pressure (OPEP) intensity level to control the amount of airflow enhancement at the patient's mouth that is input to motor drive amplifier 72. Based upon a control signal from summing junction 76, motor drive amplifier 72 operates linear motor 82 causing diaphragm 80 of linear motor 82 to oscillate air within air chamber 84. The control signal is based upon the PEP feedback signal from low pass filter 92 (which represents the steady state pressure in chamber 84) and the signal waveform from phase shift network 54 through OPEP potentiometer 60. The oscillatory waveform created in air chamber 84 is selected with the desired phase, intensity, and wave shape to perform the needed task. Linear motor 82 is not restricted to a sinusoidal waveform and can move in any complex pattern. Other embodiments of the invention may use other components to produce the same waveforms as linear motor 82 such as a solenoid or a motor driven cam mechanism.

Air pressure from air chamber 84 is measured by sampling tube 86 and pressure transducer 88 relative to atmospheric pressure. The electrical signal generated by pressure transducer 88 is filtered by low pass filter 92, which has such a low frequency cutoff that the output from low pass filter 92 is essentially the average pressure in air chamber 84 produced by filtering out the effects of linear motor 82 and then carried on line 96. This PEP feedback signal is carried to the minus (−) input of comparator error amplifier 94 by line 98. PEP level potentiometer 100 selects a Positive Expiratory Pressure (PEP) level which is fed into the plus (+) input of comparator error amplifier 94 via line 102. The PEP level is adjusted by PEP level potentiometer 100 to match the mean pressure exerted on the patient's chest wall by chest wall force applicator 12a. The output of comparator error amplifier 94 activates blower controller motor driver 104 which maintains the speed of blower 106. Since blower 106 communicates with air chamber 84 through tube 108a, the steady state pressure bias is regulated within air chamber 84. Constriction 108b, within tube 108a, prevents back flow of pressure pulses to blower 106 which would effect the pressure pulsation as previously discussed. The steady state pressure bias is maintained in the patient's mouth through communication with air chamber 84 via tube 110 and mouthpiece 112.

Air pressure input mouthpiece system 12b accomplishes, in effect, a shift in the effective atmospheric pressure. An oscillatory airflow is produced that rides on a steady state pressure (which is greater than atmospheric pressure) in the mouth. The combined oscillatory pressure and steady state pressure has a waveform, intensity, and phase relationship to the chest compressions that enhances airflow through the air passages. In addition, the patient perceives no vest pressure, because the steady state pressure in the mouth and lungs is equal to and opposite the pressure from chest wall force applicator 12a, and thus, the forces counteract each other. This is very beneficial with some disease states where the external pressure on the chest from a chest wall force applicator 12a can cause considerable distress to the patient. A patient may already have difficulty breathing and would have even greater difficultly if the patient had to breathe against a force trying to compress the patient's lungs.

Air pressure input mouthpiece system 12b also provides an effective means of enhancing oscillations caused by chest wall force applicator 12a without increasing the force applied on the patient's chest. Increased force on the patient's chest would be too uncomfortable. Therefore, air pressure input mouthpiece system 12b enhances the function of chest wall force applicator 12a by oscillating the pressure at the patient's mouth in synchronism with the airflow produced by the oscillations on the chest by chest wall force applicator 12a.

Since OPEP potentiometer 60 regulates the extent to which air pressure input mouthpiece system 12b enhances airflow velocity created by chest wall force applicator 12a, it can alternatively be set to (a) increase the volume of the lungs slightly by increasing the pressure in air chamber 84 or (b) deflate the lungs by decreasing the pressure in air chamber 84. This is a beneficial function, because in some disease states the lungs need to be given greater volume. In other disease states where the lungs may be lyperinflated, it is desirable to reduce the lungs' volume.

Outlet port 114 is located a short distance from mouthpiece 112. The distance is determined by the distance 100% humidified air from mouthpiece 112 travels in one cycle. This allows the humid air from the outflow half cycles to be returned to the patient's airways during the inflow half cycles, thus preventing the airways from drying out. The positive pressure produced by blower 106 maintains a net average of airflow from blower 106 through air chamber 84 and tube 110 and out outlet port 114. Therefore, any fluids and mucus are drained out through outlet port 114 and not passed into air chamber 84 where they could cause damage. In addition, this airflow stream provides a continuous supply of fresh air for normal respiration as the much larger tidal breathing volume oscillations move fresh air from the position of outlet port 114 in tube 110 into the patient's lungs.

SECOND EMBODIMENT (FIGS. 2–4B)

Figure 2:
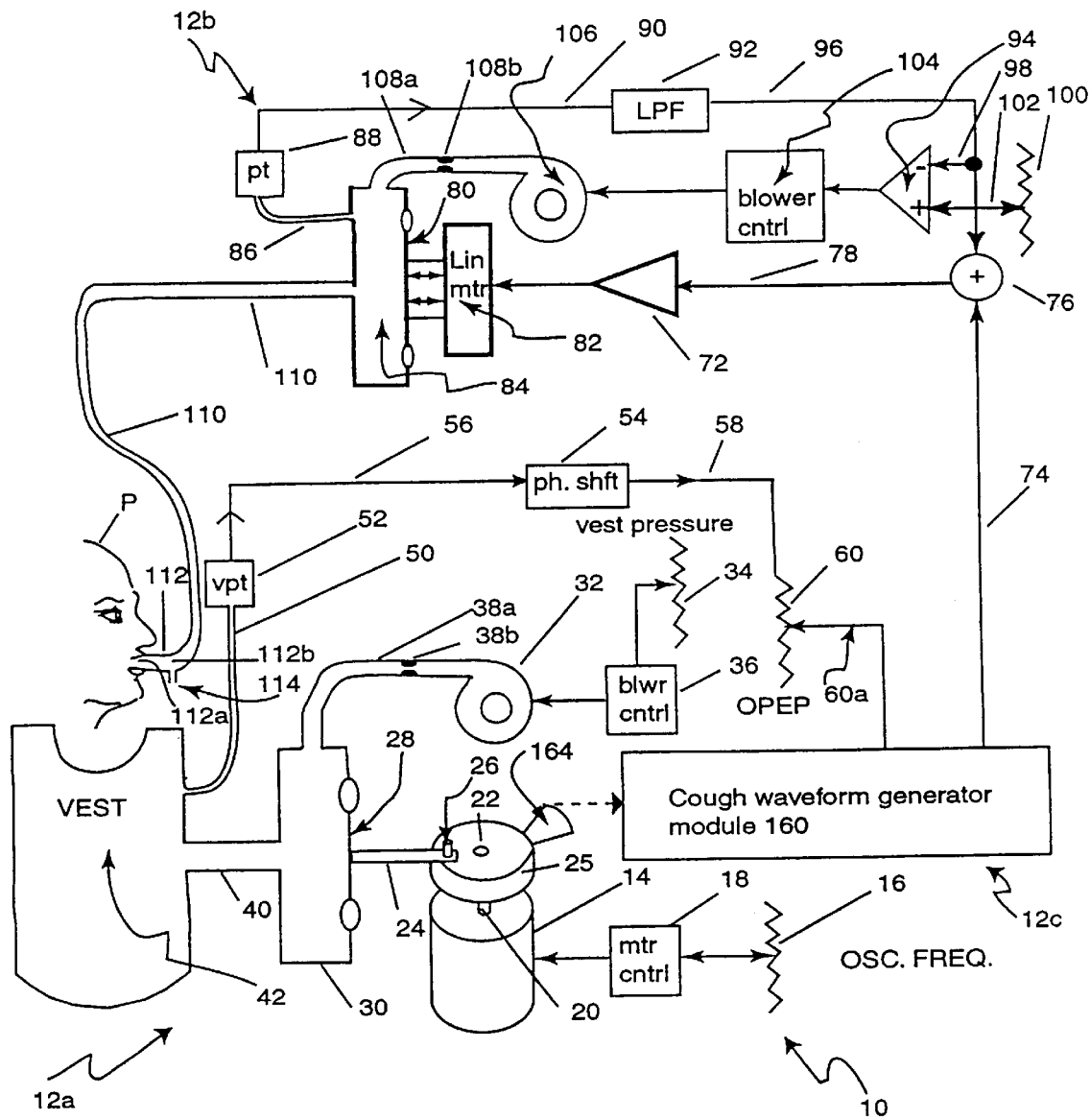
FIG. 2 is a block diagram of a second embodiment of an airway treatment apparatus which includes simulated cough inducement.
Figure 3:
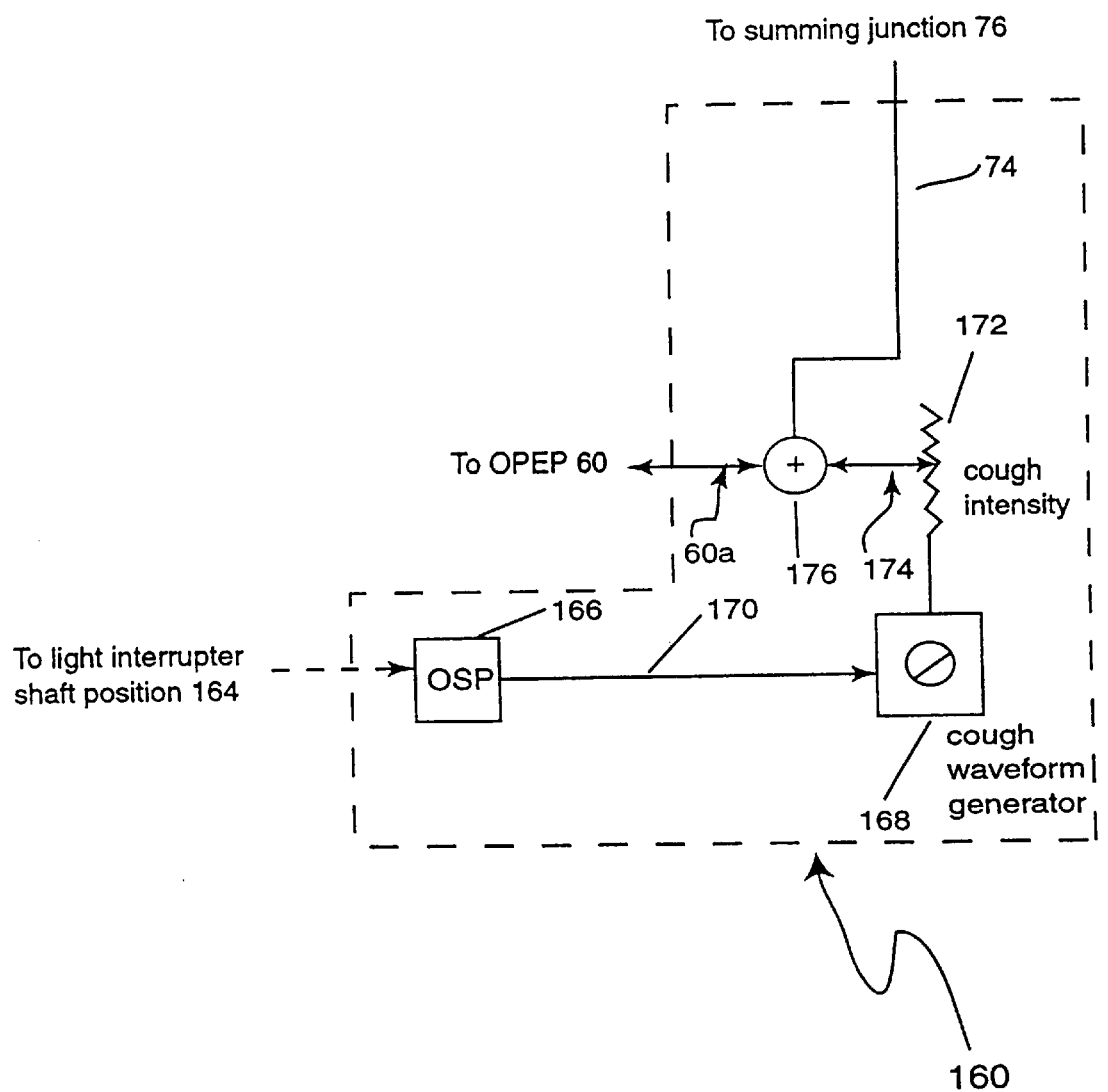
FIG. 3 is a schematic block diagram of the cough waveform generator module of FIG. 2.

FIG. 2 shows a second embodiment of apparatus 10, having a simulated cough inducer 12c, which includes cough waveform generator module 160 and light interrupter 164. The embodiment shown in FIG. 2 is generally similar to the embodiment of FIG. 1, and similar reference characters are used to designate similar elements. FIG. 3 shows a schematic block diagram of cough waveform generator module 160, which includes optical sensor processor 166, cough waveform generator 168, line 170, cough intensity potentiometer 172, line 174, and summing junction 176.

Light interrupter 164 (FIG. 2) is attached to wheel 22 and sends signals to optical sensor processor 166. These components make up a diaphragm position sensor which is connected to cough waveform generator 168 via line 170. The output of cough waveform generator 168 is connected to Cough Intensity potentiometer 172. Line 174 connects Cough Intensity potentiometer 172 with one input of summing junction 176. Another input of summing junction 176 is connected to wiper 60a of OPEP potentiometer 60. Line 74 connects the output of summing junction 176 with an input of summing junction 76. The output of summing junction 76 is connected to motor drive amplifier 72 through line 78.

In operation, the diaphragm position sensor formed by light interrupter 164 and optical sensor processor 166 produces a timing signal that triggers the start and finish of cough waveform generator 168. When oscillatory lung pressure peaks (as indicated by the position of light interrupter 164), optical sensor processor 166 activates cough waveform generator 168. Optical sensor processor 166 stops cough waveform generator 168 when oscillatory lung pressure reaches zero (as indicated by the position of light interrupter 164). Cough Intensity potentiometer 172 determines the magnitude of the signal from cough waveform generator 168, and the signal is carried to summing junction 176 via line 174. As described previously, OPEP potentiometer 60 sets the level of the OPEP waveform, and this signal is also supplied to summing junction 176. Summing junction 176 then combines the OPEP waveform signal with the cough waveform signal from cough waveform generator 168. The output of summing junction 176, which includes the cough waveform set at the desired intensity, is carried through line 74 to summing junction 76. The combined OPEP/cough signal is summed with the steady state pressure signal from low pass filter 92 and is sent to motor drive amplifier 72 along line 78.

During one phase of the cough sequence, the pressure wave from air chamber 84 causes near zero airflow out of mouthpiece 112. Simultaneously, pressure from chest wall force applicator 12a on the chest is increasing. What results is a build up of airway pressure in the lungs with very little outward flow. In the next phase, approximately when lung pressure peaks, there is a rapid increase in the flow outward from the lungs. Therefore, the flow rate while inspiring is lower than the flow rate while expiring, but the volume of air during each half cycle is equal. Since this is the pattern of a natural cough, a cough is simulated with each oscillatory cycle, which can be up to 20 times/second.

In one embodiment, simulated cough inducer 12c can be utilized instead of enhancing the increased airflow velocities created by chest wall force applicator 12a using sinusoidal enhancement with air pressure input mouthpiece system 12b. In another embodiment, OPEP potentiometer 60 (which adjusts the magnitude of sinusoidal enhancement) and Cough Intensity potentiometer 172 (which controls the magnitude of the cough waveform) can be combined in any proportion at summing junction 176 to provide the desired effect.

FIGS. 4a and 4b illustrate the cough sequence. FIGS. 4a and 4b show pressure from chest wall force applicator 12a on the patient's chest and airflow from the patient's mouth during a cough sequence. FIG. 4a shows one oscillatory cycle and FIG. 4b shows multiple oscillatory cycles. The sinusoidal wave is a vest pressure waveform 180 and the jagged waveform 182 is airflow at the patient's mouth. The high frequency oscillations of the airflow waveform are caused by resonance of the tubes within the present invention and the patient's air passages and are of no consequence.

Line 184, of FIG. 4a, indicates zero airflow. When the waveform is above this line, the patient is inspiring and when below the line, the patient is expiring. Vest pressure increases downward from line 186. Prior to about point 188, airflow is about zero. This is the period of building pressure in the lungs and is equivalent to the glottis closing during a natural cough in order to allow pressure to build in the lungs. At about point 188, vest pressure peaks, and airflow from the mouth is at a maximum. This coincides with the rapid increase in airflow out of the mouth when the glottis opens during a natural cough. Expiratory rate is up to 3 liters/second. Point 190 shows a gradual inspiration, as in a natural cough. Integration of the airflow waveform 182 below and above line 184 produces a net flow of zero. FIG. 4b shows the cough sequence at a different time scale illustrating multiple induced coughs.

With the present invention, even weakened individuals that cannot voluntarily cough can clear mucus from upper bronchial passages and trachea into the mouth to expectorate the mucus. Even for individuals with normal strength, coughing is an effective way of clearing mucus from airways, and therefore, this greatly enhances the mucus clearing capability of the invention.

THIRD EMBODIMENT (FIGS. 5–8C)

Figure 5:
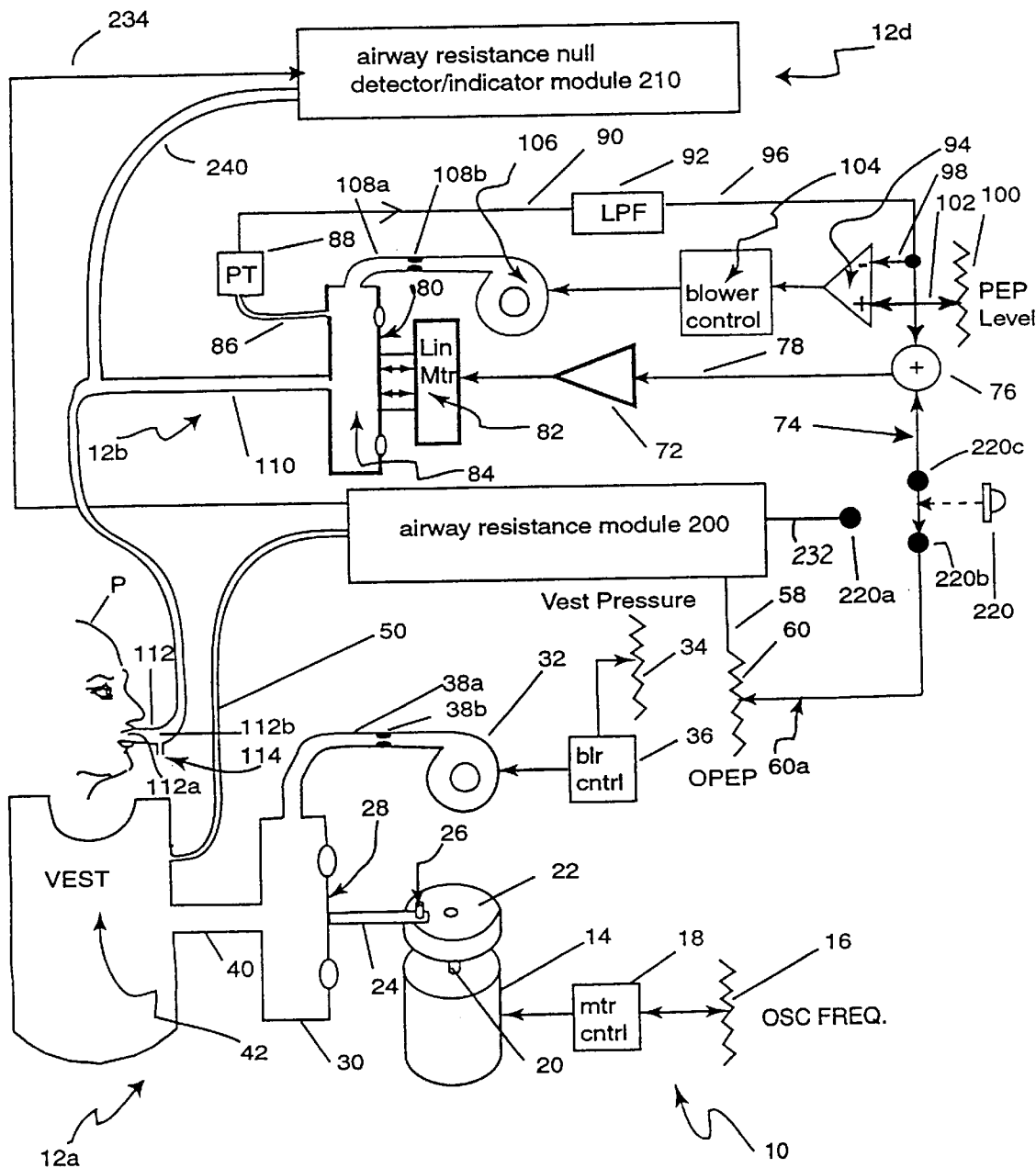
FIG. 5 is a block diagram of a third embodiment of an airway treatment apparatus which provides airway resistance measurement.
Figure 6:
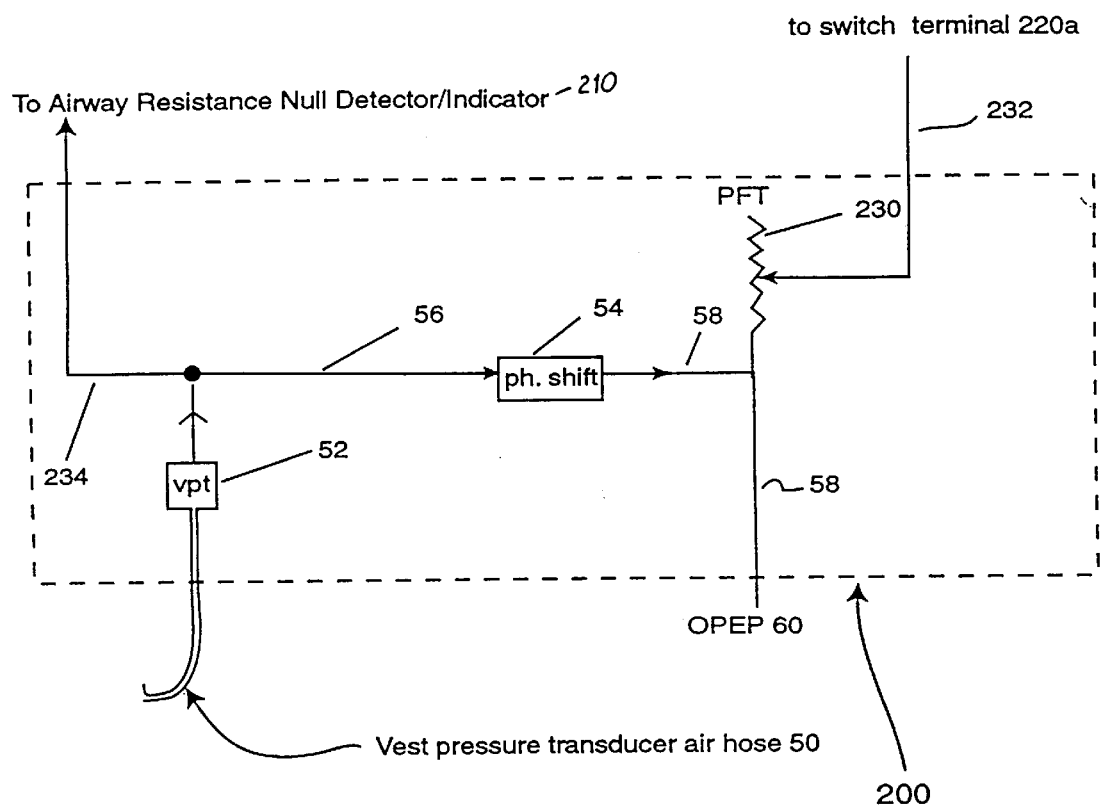
FIG. 6 is a schematic block diagram of the airway resistance module of FIG. 5.
Figure 7:
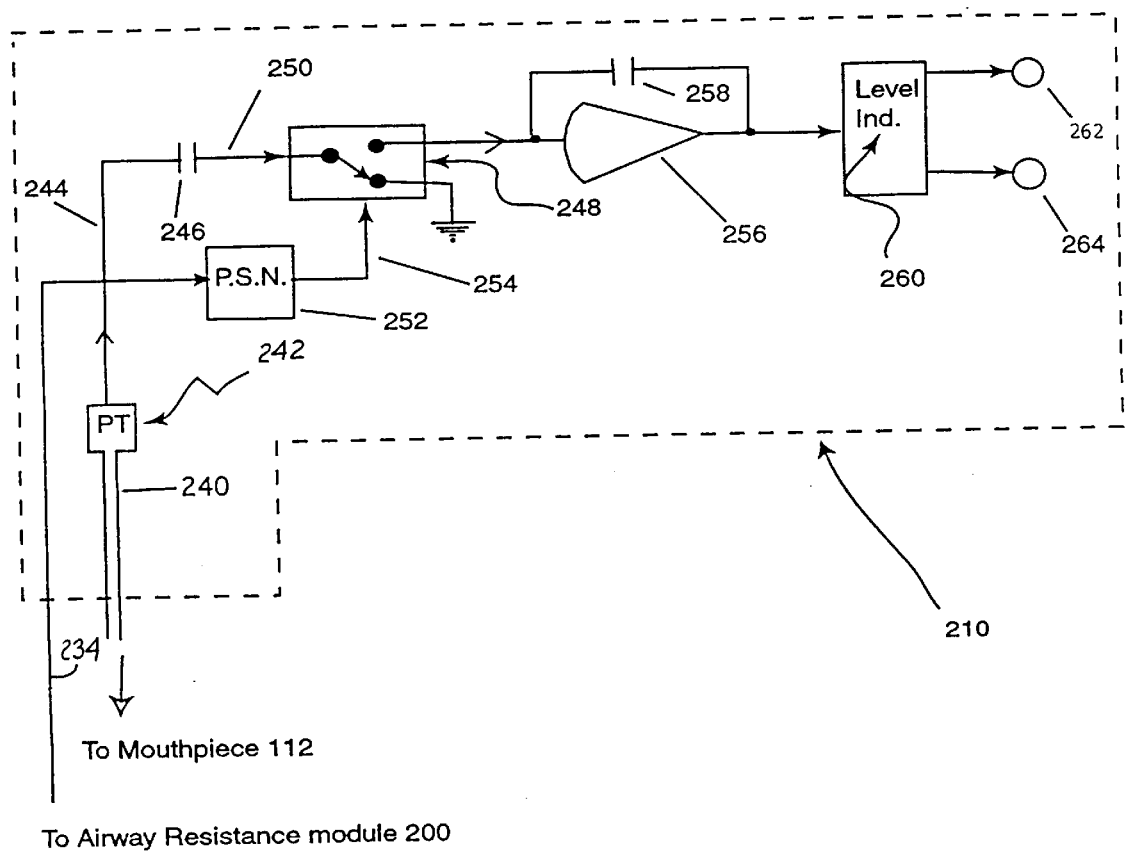
FIG. 7 is a schematic block diagram of the airway resistance null detector/indicator module of FIG. 5.

FIG. 5 shows a third embodiment of apparatus 10 which further includes airway resistance indicator 12d. The embodiment shown in FIG. 5 is generally similar to the embodiment shown in FIG. 1, and similar reference characters are used to designate similar elements. Airway resistance indicator 12d includes airway resistance module 200 (shown in FIG. 6), airway resistance null detector/indicator module 210 (shown in FIG. 7) and test switch 220 (having terminals 220a–220c).

Airway resistance module 200 (FIG. 6) includes vest pressure transducer 52, phase shift network 54, lines 56 and 58, and PFT potentiometer 230, and lines 232 and 234. Vest pressure transducer 52 is linked to inflatable vest 42 by vest sampling tube 50. Phase shift network 54 is coupled to vest pressure transducer 52 via line 56. Line 58 connects phase shift network 54 with PFT potentiometer 230, which is connected to terminal 220a of test switch 220 by line 232. Line 234 couples the output of vest pressure transducer 52 with airway resistance null detector/indicator 210.

Airway resistance null detector/indicator module 210 (FIG. 7) includes pressure tube 240, pressure transducer 242, line 244, capacitor 246, double pole switch 248, line 250, phase shift network 252, line 254, integrator 256 with integrator capacitor 258, level indicator 260, and LEDs 262 and 264. Pressure tube 240 is coupled to mouthpiece 112 and pressure transducer 242. Through line 244, the output of pressure transducer 242 is connected to capacitor 246 which is connected to double pole switch 248 via line 250. Double pole switch 248 has one output terminal connected to integrator 256 with integrator capacitor 258, and the other output terminal connected to ground. The input of level indicator 260 is connected to integrator 256, and the output of level indicator 260 is connected with and selectively drives LEDs 262 and 264. Signals from airway resistance module 200 are carried to phase shift network 252 which is connected to the control input of double pole switch 248 via line 254.

In operation, vest sampling tube 50 conveys vest pressure to vest pressure transducer 52 (FIG. 6) which converts it to an electrical signal. The electrical output signal of vest pressure transducer 52 is sent to phase shift network 54 via line 56. Phase shift network 54 compensates for delays in oscillatory pressure from chest wall force applicator 12a being transmitted as an oscillation within the patient's lungs and to the patient's mouth. The signal from phase shift network 54 (having a waveform representative of vest pressure applied by chest wall force applicator 12a) is subsequently carried by line 58 to PFT potentiometer 230 (as well as to OPEP potentiometer 60).

At the same time, pressure tube 240 samples the pressure in the patient's mouth. Transducer 242 (FIG. 7) converts this pressure to an electrical signal. The output of transducer 242 is carried to capacitor 246 via line 244. Line 250 then carries the signal from capacitor 250 to the input of double pole switch 248. Capacitor 246 removes the dc signal component from the electrical output signal of pressure transducer 242.

A vest pressure signal is a control input into double pole switch 248. Line 234 inputs the vest pressure signal from vest pressure transducer 52 (FIG. 6) to phase shift network 252, which controls the switch timing of double pole switch 248. The signal from phase shift network 252 is carried to double pole switch 248 through line 254 and switches to ground to discharge any accumulated charge on capacitor 246, which prevents a dc voltage build up.

When the compressive force of vest 42 of chest wall applicator 12a peaks, double pole switch 248 connects capacitor 246 to the input of integrator 256 to sample the mouth pressure waveform fed through capacitor 246. If the average signal output of integrator 256 indicates that the oscillatory pressure in mouthpiece 112 is less than the lung oscillatory pressure, level indicator 260 lights LED 262. If the average signal output of integrator 256 indicates that the oscillatory pressure in mouthpiece 112 is greater than the lung oscillatory pressure, level indicator 260 lights LED 264.

During, treatment, airway resistance may be checked to determine the progress of lung clearance. To accomplish this, test switch 220 is pressed so that it connects terminal 220a to terminal 220c (see FIG. 5). At this point PFT potentiometer 230 of airway resistance module 200 provides an input to motor drive amplifier 72 (through test switch 220 and summing junction 76) and controls air pressure input mouthpiece system 12b. PFT potentiometer 230 is adjusted until both LED's 262 and 264 are not lit. This is the null point of pressure within the mouth-the oscillatory air pressure waves induced by chest wall force applicator 12a are equal and opposite to the oscillatory pressure waves provided at mouthpiece 112 by air pressure input mouthpiece system 12b. The airflow and air pressure in mouthpiece 112 are at a magnitude equal to that flow caused by the oscillation pressure of chest wall force applicator 12a on the patient's chest, which is transferred to the patient's lungs and is then suppressed by the resistance of the mucus in the airways as the air flows through them on the way to the patient's mouth. The indicator knob position of PFT potentiometer 230 provides a numerical reading of the airway resistance of the patient's lungs. Using this test, progress can be checked during treatment and from one treatment to the next. All factors except airway resistance should be constant. In an alternative embodiment, a computer algorithm is used to find the null point of pressure and convert that to a numerical value for display or print out.

A common method for determining airway resistance measures air flow through a restriction over time. The problems with this method, which are solved with the present invention, are that mucus can clog the restriction, the equipment needs to be calibrated, and it is maneuver-dependent on the patient. These factors can lead to erroneous results.

FIGS. 8a, 8b, and 8c graph pressure waves from chest wall force applicator 12a (vest pressure 300) and the patient's mouth through mouthpiece 112 (mouth pressure 310) versus time. FIG. 8a is an illustration of the force from chest wall applicator at a greater pressure than the pressure at the patient's mouth created by air pressure input mouthpiece system 12b. This is the situation where LED 262 of airway resistance module 210 would light. The upper waveform 300 is the oscillatory pressure of chest wall force applicator 12a. The lower waveform 310 is the oscillatory pressure at the patient's mouth which is the sum of the oscillations from the lungs plus oscillations from the air chamber 84 traveling down tube 110.

FIG. 8b is an illustration of waveforms during the null point of pressure. Neither LED (262, 264) would light during this period. Again, the upper waveform 300 is the oscillatory pressure from chest wall force applicator 12a, and the lower waveform 310 is the pressure at the patient's mouth through mouthpiece 112. As described above, the null point of pressure is reached when the outward flow from the patient's mouth caused by air pressure input mouthpiece system 12b almost exactly equals the expiratory flow caused by the compressive force of chest wall force applicator 12a on the patient's chest. Therefore, PFT potentiometer 230, while defining the flow rate from the patient's mouth, is an analog of the airway resistance at the null point of pressure. The small pressure variations seen in the lower waveform 310 are due to imperfections in the phase angle and shape of the two pressure waves producing less than perfect cancellation. Thus, null is indicated by a minimum in the amplitude of this waveform 310.

FIG. 8c is an illustration of waveforms 300 and 310 when the pressure in mouthpiece 112 measured from tube 110 is greater than the oscillatory pressure produced by chest wall force applicator 12a. LED 264 lights in this situation. The wave shape of waveform 310 is the result of the combining of two pressure waves having unequal magnitude and phase. The oscillations on the patient's chest become out of phase by 180° compared to airflow oscillations at the patient's mouth. These FIGS. 8a–8c show that there is a null point of pressure where the two pressures cancel each other, and on either side of this point non-zero waveforms are generated.

One advantage of this system is that the null point of pressure is chosen, so no calibration sequence is required of system components. Another advantage is that it does not require any breathing maneuvers on the part of the patient. Repeatable adherence to a maneuver is necessary for standard pulmonary function testing, therefore, tests relying on breathing maneuvers may be inaccurate, or the data may not be usable.

FOURTH EMBODIMENT (FIG. 9)

Figure 9:
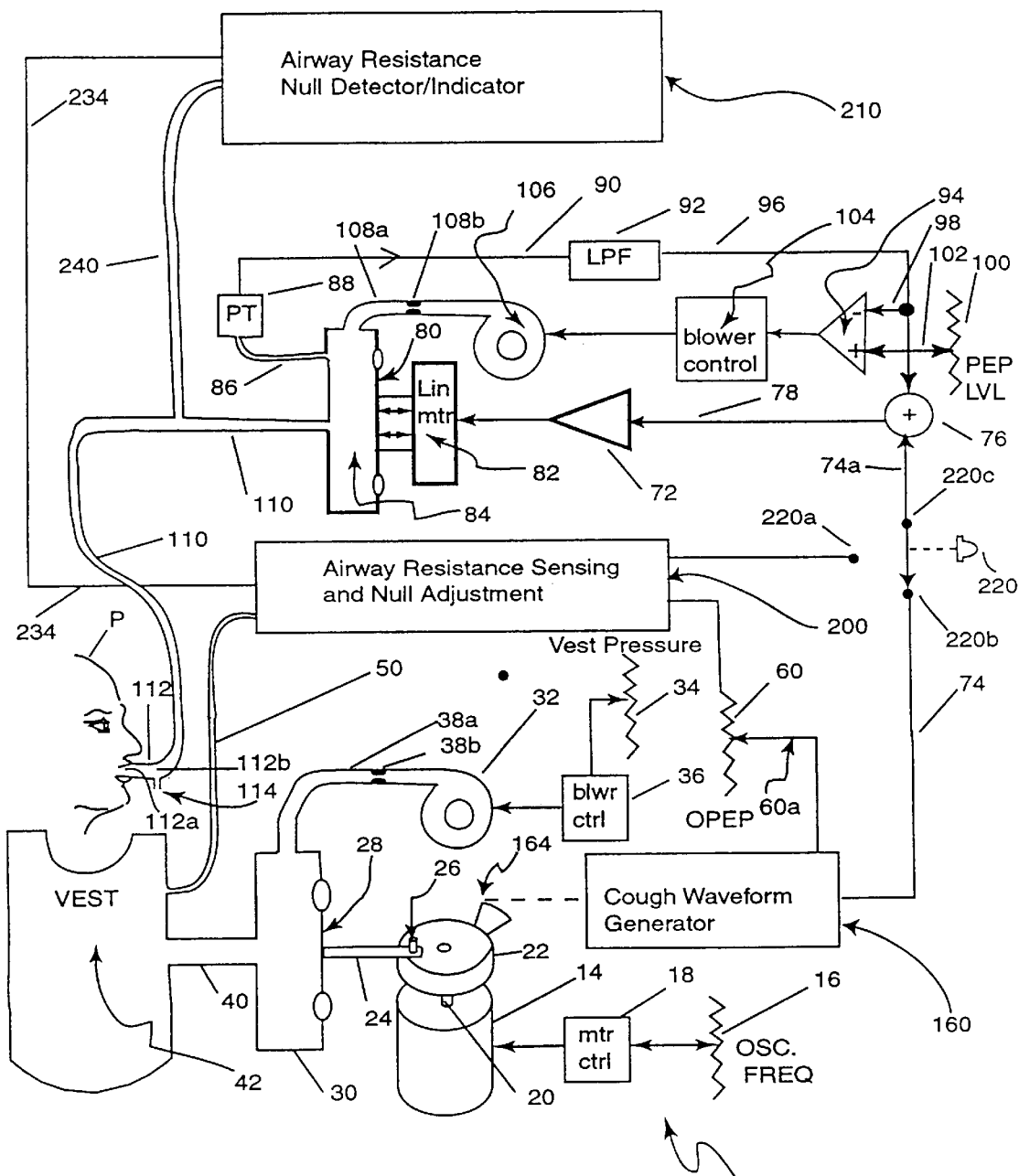
FIG. 9 is a block diagram of a fourth embodiment of an airway treatment apparatus which includes all of the features of the first, second, and third embodiments.

FIG. 9 shows a fourth embodiment of apparatus 10 which includes all of the features of the first, second and third embodiments. In this fourth embodiment, each of the systems work together to efficiently remove mucus from the patient's lungs and provide a means of determining the progress of the treatment. At the same time, patient comfort is maintained during treatment.

CONCLUSION

Airway treatment apparatus 10 performs in such a way that the patient receiving treatment perceives no external pressure on the chest which may cause discomfort depending on the disease state of the patient. Increased oscillatory airflow velocities can be achieved over prior art vest systems, which is the key to successful lung clearance. By incorporating a mechanism to simulate a cough, outcome measuring airway treatment apparatus 10 provides better lung clearance over other vest systems and induces individuals that are not able to voluntarily cough to simulate coughs.

Although the present invention has been described with reference to preferred embodiments, workers skilled in the art will recognize that changes may be made in form and detail without departing from the spirit and scope of the invention. For example, although the control systems shown in the figures use analog circuitry, other embodiments use digital logic and programmable devices (such as programmable logic arrays, microcontrollers, or microprocessors) to provide the control functions.

What is claimed is:

1. A chest wall oscillation method for airway treatment of a patient having a chest and a mouth, the method comprising:

applying an oscillating compressive force to the patient's chest which includes a steady state force component and an oscillating force component; and supplying air pressure to a mouthpiece in communication with the patient's mouth in a synchronized relationship to the oscillating compressive force to induce a simulated cough during a compressive force oscillatory cycle.

2. The method of claim 1 wherein supplying air pressure includes providing an oscillating air pressure component and a steady state air pressure component.

3. The method of claim 2 wherein the steady state air pressure component tends to counteract the steady state force component of the oscillating compressive force.

4. The method of claim 3 wherein the steady state air pressure component exerted to the patient's chest approximately balances the steady state force component of the oscillating compressive force exerted on the patient's chest.

5. The method of claim 2 wherein the oscillating air pressure component is produced as a function of the oscillating force component.

6. The method of claim 5 wherein the oscillating air pressure componet is synchronized with the oscillating force component so that the oscillating air pressure component enhances airflow produced by the oscillating compressive force.

7. The method of claim 1 wherein the mouthpiece includes a mouthpiece chamber having a mouth port, an outlet port, and an air supply port through which the air pressure is supplied to the mouthpiece.

8. The method of claim 7 wherein air pressure supplied to the air supply port of the mouthpiece produces a flow of air to the air supply port and out the outlet port.

9. A chest wall oscillating method for airway of a patient having lungs, a chest, and a mouth, the method comprising:
   applying an oscillating compressive force to the patient's chest which includes a steady state force component and an oscillating force component; and
   supplying air pressure to a mouthpiece in communication with the patient's mouth which creates a buildup of airway pressure in the patient's lungs with very little outward flow of air from the patient's lungs to the mouthpiece, followed by a rapid increase of flow outward from the lungs to the mouthpiece when the oscillating compressive force is at about a maximum force.

10. A chest wall oscillation method for airway treatment of a patient having a chest, lungs and a mouth, the method comprising:
    applying an oscillating compressive force to the patient's chest; and
    supplying an oscillating air pressure to a mouthpiece in communication with the patient's mouth so that the oscillating air pressure enhances airflow to and from the patient's lungs produced by the oscillating compressive force and induces a simulated cough.

11. A chest wall oscillating method for airway treatment of a patient having a chest and a mouth, the method comprising:
    applying an oscillating compressive force to the patient's chest;
    supplying air pressure to a mouthpiece positioned in the patient's mouth; and
    coordinating the oscillating compressive force and the air pressure supplied to the mouthpiece so that air flow out of the patient's mouth is for a shorter duration than air flow into the patient's mouth.

12. A method of airway treatment of a patient having a chest and a mouth by inducing movement of mucus by chest wall oscillation, the method comprising:
    applying an oscillating compressive force to the patient's chest; and
    supplying air pressure to a mouthpiece in communication with the patient's mouth to induce a simulated cough.

13. A chest wall oscillation method for airway treatment of a patient having lungs, a chest and a mouth, the method comprising:
    applying an oscillating compressive force to the patient's chest; and
    supplying air pressure to a mouthpiece in communication with the patient's mouth to create a buildup of airway pressure in the patient's lungs with very little outward flow of air from the patient's lungs to the mouthpiece followed by a rapid increase of flow outward from the lungs to the mouthpiece when the oscillating compressive force applied is at about a maximum force.

14. A chest wall oscillation airway treatment system comprising:
    a chest wall force applicator for applying an oscillating compressive force to a chest of a patient;
    a mouthpiece having a mouth port, an outlet port, and an air supply port;
    an air pressure supply connected to the air supply port; and
    a control system which coordinates operation of the chest wall force applicator and the air pressure supply to induce a simulated cough.

15. The system of claim 14 wherein the control system causes supplied air pressure to the mouthpiece to create a buildup of air pressure in lungs of the patient with very little outward flow of air from the lungs to the mouthpiece followed by a rapid increase of flow outward from the lungs to the mouthpiece when the oscillating compressive force being applied to the patient's chest is at about a maximum force.

16. The system of claim 14 wherein the chest wall force applicator produces an oscillating compressive force having a steady state force component and an oscillating force component.

17. The system of claim 16 wherein the air pressure supply provides air to the air supply port according to a control signal representing an air pressure waveform having a steady state air pressure component and an oscillatory air pressure component.

18. The system of claim 17 wherein the control system causes the steady state air pressure component to at least cancel the steady state force component.

19. The system of claim 17 wherein the control system causes the oscillatory air pressure component to be synchronized with the oscillating force component so that airflow to and from lungs of the patient produced by the oscillating compressive force is enhanced.

20. The system of claim 17 wherein air supplied to the air supply port of the mouthpiece produces a flow of air to the air supply port and out the outlet port.

21. The system of claim 14 wherein the control system coordinates operation of the chest wall force applicator and the air pressure supply to induce a series of simulated coughs.

22. A chest wall oscillation method for removal of mucus from a lung of a patient, the method comprising:
    applying an oscillating compressive force to a chest of the patient which includes a steady state force component and an oscillating force component; and
    supplying air pressure to a mouthpiece in communication with a mouth of the patient in a synchronized relationship to the oscillating compressive force to induce a simulated cough to enhance mucus movement.

23. The method of claim 22 wherein supplying air pressure includes providing an oscillating air pressure component and a steady state air pressure component.

24. The method of claim 23 wherein the steady state air pressure component tends to counteract the steady state force component of the oscillating compressive force.

25. The method of claim 24 wherein the steady state air pressure component exerted to the patient's chest approximately balances the steady state force component of the oscillating compressive force exerted on the patient's chest.

26. The method of claim 23 wherein the oscillating air pressure component is produced as a function of the oscillating force component.

27. The method of claim 26 wherein the oscillating air pressure component is synchronized with the oscillating force component so that the oscillating air pressure component enhances airflow produced by the oscillating compressive force.

28. The method of claim 22 wherein the mouthpiece includes a mouthpiece chamber having a mouth port, an outlet port, and an air supply port through which the air pressure is supplied to the mouthpiece.

29. The method of claim 28 wherein air pressure supplied to the air supply port of the mouthpiece produces a flow of air to the air supply port and out the outlet port.

30. A chest wall oscillating method for removal of mucus from a lung of a patient, the method comprising:
applying an oscillating compressive force to a chest of the patient which includes a steady state force component and an oscillating force component; and
supplying air pressure to a mouthpiece in communication with a mouth of the patient which creates a buildup of airway pressure in the lung of the patient with very little outward flow of air from the lung to the mouthpiece, followed by a rapid increase of flow outward from the lung to the mouthpiece when the oscillating compressive force is applied at about a peak force.

31. A method for removal of mucus from a lung of a patient, the method comprising:
applying an oscillating compressive force to a chest of the patient; and
supplying an oscillating air pressure to a mouthpiece in communication with a mouth of the patient so that the oscillating air pressure enhances airflow to and from the lung of the patient produced by the oscillating compressive force and induces a simulated cough to enhance mucus removal.

32. A method for removal of mucus from a lung of a patient, the method comprising:
applying an oscillating compressive force to a chest of the patient;
supplying air pressure to a mouthpiece positioned in a mouth of the patient; and
coordinating the oscillating compressive force and the air pressure supplied to the mouthpiece so that air flow out of the patient's mouth is for a shorter duration than air flow into the patient's mouth.

33. A method of inducing movement of mucus by chest wall oscillation, the method comprising:
applying an oscillating compressive force to a chest of a patient; and
supplying air pressure to a mouthpiece in communication with a mouth of the patient to induce a simulated cough which causes mucus movement.

34. The method of claim 33 wherein supplying the air pressure induces a series of simulated coughs.

35. A method for removal of mucus from a lung of a patient, the method comprising:
applying an oscillating compressive force to a chest of the patient; and
supplying air pressure to a mouthpiece in communication with a mouth of the patient to create a buildup of airway pressure in the lung of the patient with very little outward flow of air from the lung to the mouthpiece followed by a rapid increase of flow outward from the lung to the mouthpiece when the oscillating compressive force applied to produce mucus movement is at about a maximum force.

36. A chest wall oscillation system for removal of mucus from a lung of a patient, the system comprising:
a chest wall force applicator for applying an oscillating compressive force to a chest of the patient;
a mouthpiece having a mouth port, an outlet port, and an air supply port;
an air pressure supply connected to the air supply port; and
a control system which coordinates operation of the chest wall force applicator and the air pressure supply to induce a simulated cough which enhances mucus movement.

37. The system of claim 36 wherein the control system causes supplied air pressure to the mouthpiece to create a buildup of air pressure in the patient's lung with very little outward flow of air from the patient's lung to the mouthpiece followed by a rapid increase of flow outward from the lung to the mouthpiece when the oscillating compressive force is about a maximum force.

38. The system of claim 36 wherein the chest wall force applicator produces an oscillating compressive force having a steady state force component and an oscillating force component.

39. The system of claim 38 wherein the air pressure supply provides air to the air supply port according to a control signal representing an air pressure waveform having a steady state air pressure component and an oscillatory air pressure component.

40. The system of claim 39 wherein the control system causes the steady state air pressure component to at least cancel the steady state force component.

41. The system of claim 39 wherein the control system causes the oscillatory air pressure component to be synchronized with the oscillating force component so that airflow is enhanced.

42. The system of claim 39 wherein air supplied to the air supply port of the mouthpiece produces a flow of air to the air supply port and out the outlet port.

43. A chest wall oscillation method of mucus removal, the method comprising:
applying an oscillating chest wall compressive force which includes a steady state force component and an oscillating force component; and
supplying air pressure to a mouthpiece in a synchronized relationship to the oscillating chest wall compressive force to induce a simulated cough.

44. The method of claim 43 wherein supplying air pressure includes providing an oscillating air pressure component and a steady state air pressure component.

45. The method of claim 44 wherein the steady state air pressure component tends to counteract the steady state force component of the oscillating chest wall compressive force.

46. The method of claim 45 wherein the steady state air pressure component exerted to the patient's chest approximately balances the oscillating chest wall compressive force.

47. The method of claim 44 wherein the oscillating air pressure component is produced as a function of the oscillating force component.

48. The method of claim 43 wherein the oscillating air pressure component is synchronized with the oscillating force component so that the oscillating air pressure component enhances airflow produced by the oscillating chest wall compressive force.

49. The method of claim 43 wherein the mouthpiece includes a mouthpiece chamber having a mouth port, an outlet port, and an air supply port through which the air pressure is supplied to the mouthpiece.

50. The method of claim 49 wherein air pressure supplied to the air supply port of the mouthpiece produces a flow of air to the air supply port and out the outlet port.

51. The method of claim 43 wherein supplying the air pressure in a synchronized relationship to the oscillating chest wall compressive force induces a series of simulated coughs.

52. A chest wall oscillating method for mucus removal, the method comprising:
    applying an oscillating chest wall compressive force which includes a steady state force component and an oscillating force component; and
    supplying air pressure to a mouthpiece which creates a buildup of airway pressure with very little outward flow of air to the mouthpiece, followed by a rapid increase of flow outward to the mouthpiece when the oscillating chest wall compressive force is at about a maximum force to produce a mucus moving simulated cough.

53. A chest wall oscillation method for mucus removal, the method comprising:
    applying an oscillating chest wall compressive force; and
    supplying an oscillating air pressure to a mouthpiece so that the oscillating air pressure enhances airflow produced by the oscillating chest wall compressive force and induces a mucus moving simulated cough.

54. A chest wall oscillating method for mucus removal, the method comprising:
    applying an oscillating chest wall compressive force;
    supplying air pressure to a mouthpiece; and
    coordinating the oscillating chest wall compressive force and the air pressure supplied to the mouthpiece so that air flow out of a mouth of a patient is for a shorter duration than air flow into the mouth to induce mucus movement.

55. A method of inducing movement of mucus by chest wall oscillation, the method comprising:
    applying an oscillating chest wall compressive force; and
    supplying air pressure to a mouthpiece to induce a chest wall simulated cough.

56. A chest wall oscillation method for mucus removal, the method comprising:
    applying an oscillating chest wall compressive force; and
    supplying air pressure to a mouthpiece to create a buildup of airway pressure with very little outward flow of air followed by a rapid increase of flow outward to the mouthpiece when the oscillaing chest wall compressive force is at about a maximum force to enhance mucus removal.

57. A chest wall oscillation system for mucus removal, the system comprising:
    a chest wall force applicator for applying an oscillating chest wall compressive force;
    a mouthpiece having a mouth port, an outlet port, and an air supply port;
    an air pressure supply connected to the air supply port; and
    a control system which coordinates operation of the chest wall force applicator and the air pressure supply to induce a mucus moving series of simulated coughs.

58. The system of claim 57 wherein the control system causes supplied air pressure to the mouthpiece to create a buildup of air pressure with very little outward flow of air to the mouthpiece followed by a rapid increase of flow outward to the mouthpiece.

59. The system of claim 57 wherein the chest wall force applicator produces an oscillating chest wall compressive force having a steady state force component and an oscillating force component.

60. The system of claim 59 wherein the air pressure supply provides air to the air supply port according to a control signal representing an air pressure waveform having a steady state air pressure component and an oscillatory air pressure component.

61. The system of claim 60 wherein the control system causes the steady state air pressure component to at least cancel the steady state force component.

62. The system of claim 60 wherein the control system causes the oscillatory air pressure component to be synchronized with the oscillating force component so that airflow is enhanced.

63. The system of claim 60 wherein air supplied to the air supply port of the mouthpiece produces a flow of air to the air supply port and out the outlet port .

* * * * *

UNITED STATES PATENT AND TRADEMARK OFFICE
CERTIFICATE OF CORRECTION

PATENT NO. : 6,415,791 B1
DATED : July 9, 2002
INVENTOR(S) : Nicholas P. Van Brunt et al.

It is certified that error appears in the above-identified patent and that said Letters Patent is hereby corrected as shown below:

<u>Column 4,</u>
Line 8, delete "oscillatory' air", insert -- oscillatory air --
Line 24, delete "ensured", insert -- sensed --

<u>Column 6,</u>
Line 12, delete "lyperinflated", insert -- hyperinflated --

<u>Column 9,</u>
Line 10, delete "During,", insert -- During --

<u>Column 11,</u>
Line 29, delete "airway", insert -- airway treatment --

<u>Column 13,</u>
Line 33, delete "ofthe", insert -- of the --

Signed and Sealed this

Third Day of June, 2003

JAMES E. ROGAN
*Director of the United States Patent and Trademark Office*